US010294784B2

(12) United States Patent
Gisolf et al.

(10) Patent No.: US 10,294,784 B2
(45) Date of Patent: May 21, 2019

(54) SYSTEMS AND METHODS FOR CONTROLLING FLOW RATE IN A FOCUSED DOWNHOLE ACQUISITION TOOL

(71) Applicant: Schlumberger Technology Corporation, Sugar Land, TX (US)

(72) Inventors: Adriaan Gisolf, Houston, TX (US); Kai Hsu, Sugar Land, TX (US); Yong Chang, Sugar Land, TX (US); Youxiang Zuo, Burnaby (CA); Ryan Sangjun Lee, Sugar Land, TX (US); Ashers Partouche, Katy, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 395 days.

(21) Appl. No.: 14/956,338

(22) Filed: Dec. 1, 2015

(65) Prior Publication Data

US 2017/0152743 A1    Jun. 1, 2017

(51) Int. Cl.
*E21B 49/08* (2006.01)
*E21B 49/10* (2006.01)
*G01N 1/14* (2006.01)
*E21B 47/12* (2012.01)

(52) U.S. Cl.
CPC ............ *E21B 49/081* (2013.01); *E21B 49/10* (2013.01); *G01N 1/14* (2013.01); *E21B 47/12* (2013.01); *E21B 2049/085* (2013.01)

(58) Field of Classification Search
CPC .................................................. E21B 49/081
See application file for complete search history.

(56) References Cited

U.S. PATENT DOCUMENTS

| 6,729,400 B2 | 5/2004 | Mullins et al. |
| 6,964,301 B2 | 11/2005 | Hill et al. |
| 7,028,773 B2 | 4/2006 | Fujisawa et al. |
| 8,555,968 B2 | 10/2013 | Zazovsky et al. |

(Continued)

FOREIGN PATENT DOCUMENTS

WO    2012094007 A2    7/2012

OTHER PUBLICATIONS

Hammond, "One- and Two-Phase Flow During Fluid Sampling by a Wireline Tool", Transport in Porous Media 6, Kluwer Academic Publishers, Netherlands, 1991, pp. 299-330.

(Continued)

*Primary Examiner* — Clayton E. LaBalle
*Assistant Examiner* — Dennis Hancock
(74) *Attorney, Agent, or Firm* — Michael Dae

(57) ABSTRACT

A method includes operating a downhole acquisition tool including a guard probe and a sample probe in a wellbore that contains a fluid that includes a native reservoir fluid and a contaminant. The method also includes receiving a first portion of fluid into the guard probe and a second portion of fluid into the sample probe, estimating a contamination level of the first or second portions based on a fluid property of the respective first and second portions, determining an initial guard flow rate of the first portion, determining an initial sample flow rate of the second portion, using a processor to adjust a guard flow rate of the second portion over pump time after the contamination level of the first portion is at or below a contamination level threshold, and adjust a sample flow rate of the first portion based on the adjusted guard flow rate and total flowrate.

23 Claims, 8 Drawing Sheets

(56) References Cited

U.S. PATENT DOCUMENTS

| | | |
|---|---|---|
| 8,805,617 B2 | 8/2014 | Zuo et al. |
| 8,904,857 B2 | 12/2014 | Tustin et al. |
| 2003/0145988 A1 | 8/2003 | Mullins et al. |
| 2004/0000400 A1 | 1/2004 | Fujisawa et al. |
| 2005/0182566 A1 | 8/2005 | DiFoggio |
| 2006/0000603 A1 | 1/2006 | Zazovsky et al. |
| 2007/0238180 A1 | 10/2007 | DiFoggio et al. |
| 2013/0025855 A1 | 1/2013 | Glattetre et al. |
| 2014/0116776 A1 | 5/2014 | Marx et al. |
| 2014/0180591 A1 | 6/2014 | Hsu et al. |
| 2015/0135814 A1 | 5/2015 | Zuo et al. |
| 2015/0142321 A1 | 5/2015 | Gisolf et al. |
| 2015/0226059 A1 | 8/2015 | Zuo et al. |
| 2015/0308264 A1 | 10/2015 | Zuo et al. |

OTHER PUBLICATIONS

Mullins, et al., "Real-Time Determination of Filtrate Contamination During Openhole Wireline Sampling by Optical Spectroscopy", SPE63071, SPE Annual Technical Conference and Exhibition, Dallas, Texas, USA, Oct. 1-4, 2000, 13 pages.

Mullins, et al., "Real-Time Quantification of OBM Filtrate Contamination During Openhole Wireline Sampling by Optical Spectroscopy", SWPLA 41st Annual Logging Symposium, Jun. 4-7, 2000, 10 pages.

Hsu, et al., "Multichannel Oil-Base Mud Contamination Monitoring Using Downhole Optical Spectrometer", SWPLA 49th Annual Logging Symposium, Edinburgh, Scotland, May 25-28, 2008, 13 pages.

International Search Report and Written Opinion issued in the related PCT Application PCT/US2016/064276, dated Feb. 16, 2017 (10 pages).

Mccain, "The Properties of Petroleum Fluids, 2nd Edition", PennWell Publishing, 1990, pp. 444-450.

Villareal, et al., "Characterization of Sampling-While-Drilling Operations", SPE 128249, IADC/SPE Drilling Conference and Exhibition, New Orleans, Louisiana, USA, Feb. 2-4, 2010.

Zuo, et al., "A New Method for OBM Decontamination in Downhole Fluid Analysis", IPTC 16524—6th International Petroleum Technology Conference, Beijing, China, Mar. 26-28, 2013.

SYSTEMS AND METHODS FOR CONTROLLING FLOW RATE IN A FOCUSED DOWNHOLE ACQUISITION TOOL

BACKGROUND

This disclosure relates to reducing sample bottle filling time of formation fluids in downhole fluid analysis.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Reservoir fluid analysis may be used in a wellbore in a geological formation to locate hydrocarbon-producing regions in the geological formation, as well as to manage production of the hydrocarbons in these regions. A downhole acquisition tool may carry out reservoir fluid analysis by drawing in formation fluid and testing the formation fluid downhole or collecting a sample of the formation fluid to bring to the surface. Although native reservoir fluid (e.g., oil, gas, or water) from a hydrocarbon reservoir in the geological formation may be the fluid of interest for reservoir fluid analysis, fluids other than the native reservoir fluid may contaminate the native reservoir fluid. As such, the formation fluid obtained by the downhole acquisition tool may contain extraneous materials other than pure native reservoir fluid. Drilling muds, for example, may be used in drilling operations and may invade the formation and mix with the native reservoir fluid. The formation fluid drawn from the wellbore thus may be a mixture of native reservoir fluid and drilling mud filtrate.

In downhole fluid analysis, the formation fluid may be pumped through one or more probes of the downhole acquisition tool. Over time (or as pump-out volume increases), the amount of the drilling mud filtrate in the formation fluid may decrease. Once the amount of drilling mud filtrate in the formation fluid reaches a desired level, the downhole acquisition tool may collect a sample of the formation fluid that is representative of the native formation fluid. Of certain concern is an amount of time it takes to fill a sample bottle with the formation fluid downhole after cleanup of the one or more probes of the downhole acquisition tool has been reached (e.g., after the amount of drilling mud filtrate reaches the desired level). For example, a flow rate of the formation fluid through the one or more probes may be continuously decreased once cleanup is achieved to maintain contamination levels below the desired threshold. Accordingly, the amount of time to fill the sample bottle with the formation fluid at the decreased flow rate may be undesirably long.

SUMMARY

This summary is provided to introduce a selection of concepts that are further described below in the detailed description. This summary is not intended to identify key or essential features of the subject matter described herein, nor is it intended to be used as an aid in limiting the scope of the subject matter described herein. Indeed, this disclosure may encompass a variety of aspects that may not be set forth below.

In one example, a method includes operating a downhole acquisition tool including a guard probe and a sample probe in a wellbore in a geological formation. The wellbore or the geological formation, or both contains a fluid that includes a native reservoir fluid of the geological formation and a contaminant. The method also includes receiving a first portion of the fluid into the guard probe and a second portion of the fluid into the sample probe, estimating a contamination level of the first portion of the fluid, the second portion of the fluid, or a combination thereof based on a fluid property of the respective first and second portions of the fluid as measured by the downhole acquisition tool, determining an initial guard flow rate of the first portion of fluid through the guard probe, determining an initial sample flow rate of the second portion of fluid through the sample probe, using a processor to adjust a guard flow rate of the second portion of the fluid through the guard probe over pump time after the contamination level of the first portion of the fluid is at or below a contamination level threshold, based on the initial guard flow rate and the estimated contamination level of the first and second portion of the fluid, and adjust a sample flow rate of the first portion of the fluid through the sample probe based on the adjusted guard flow rate and the total flowrate.

In another example, a downhole fluid testing system includes a downhole acquisition tool housing that may be moved into a wellbore in a geological formation. The wellbore or the geological formation, or both, contains a fluid that includes a native reservoir fluid of the geological formation and a contaminant. The system also includes a plurality of sensors disposed in the downhole acquisition tool housing that may analyze portions of a first portion of the fluid and a second portion of the fluid and obtain sets of fluid properties of the first and second portions of the fluid; a guard probe that may flow the first portion of the fluid at a guard flow rate, a sample probe that may flow the second portion of the fluid at a sample flow rate; and a data processing system that may adjust the guard flow rate over pump time of the fluid after the contamination level of the first portion of the fluid is at or below a contamination level threshold based on the fluid properties of the first and second portion of the fluid and an initial guard flow rate, an initial sample flow rate, or both; and adjust the sample flow rate based on the adjusted guard flow rate and the total flow rate.

In another example, one or more tangible, non-transitory, machine-readable media including instructions to receive a plurality of fluid parameters of a first portion and a second portion of a fluid as analyzed by a downhole acquisition tool in a wellbore in a geological formation. The wellbore or the geological formation, or both, contains the fluid and the fluid includes a mixture of native reservoir fluid of the geological formation and a contaminant. The one or more tangible, non-transitory, machine-readable media also includes instructions to determine an initial guard flow rate of the first portion of the fluid flowing through a guard probe of the downhole acquisition tool, determine an initial sample flow rate of the second portion of the fluid flowing through a sample probe of the downhole acquisition tool, determine a guard flow rate of the first portion of the fluid over pump time based on a contamination level of the second portion of the fluid and the initial guard flow rate; and adjust a sample flow rate of the second portion of the fluid based on a relationship between the guard flow rate and a total flow rate of the fluid through the downhole acquisition tool when the contamination level of the first portion of the fluid is at or below a contamination level threshold.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

Figure 1:
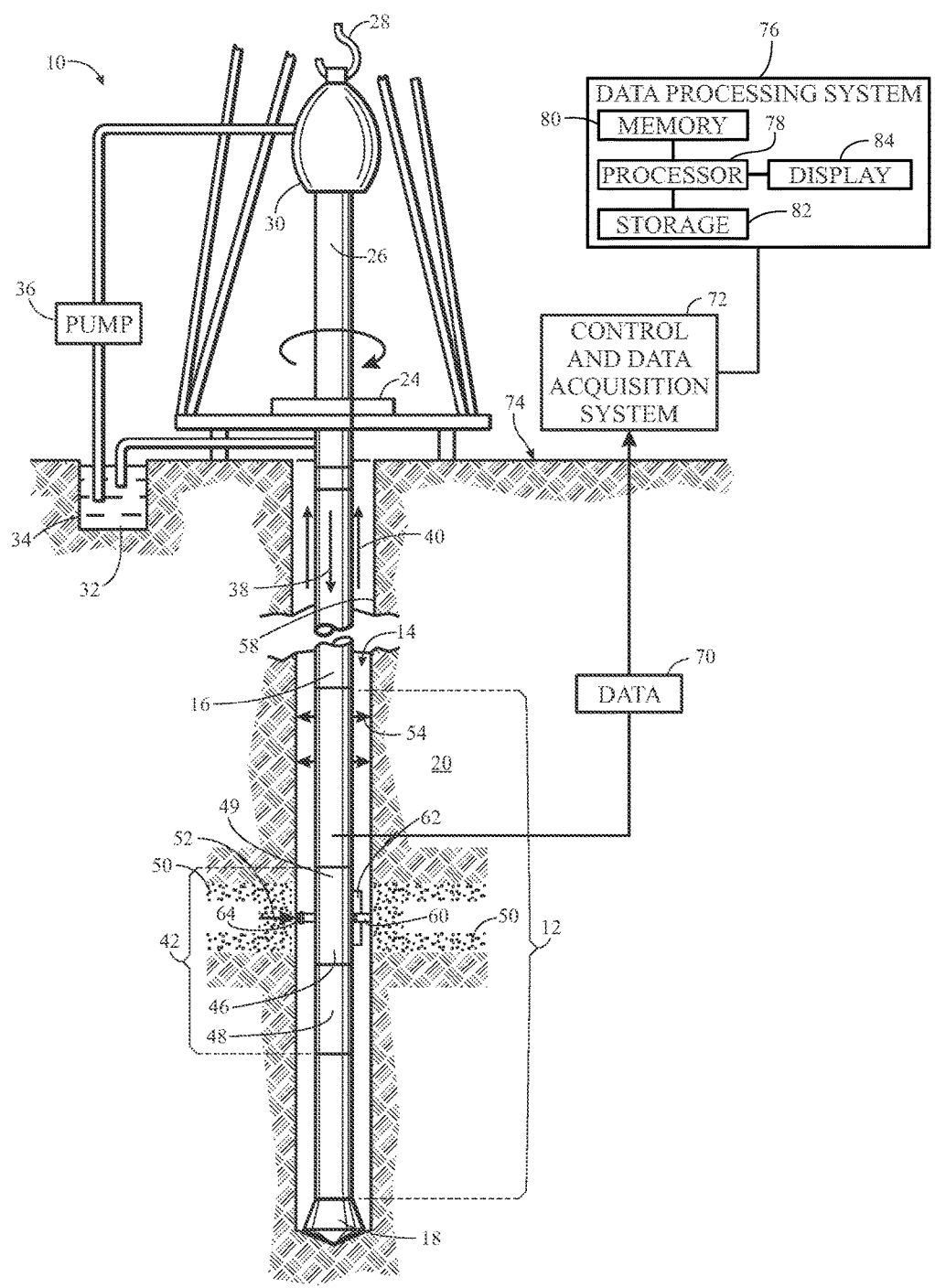
FIG. 1 is a schematic diagram of a wellsite system that may employ downhole fluid analysis methods for determining mud contamination in a formation fluid, in accordance with an embodiment.

One or more specific embodiments of the present disclosure will be described below. These described embodiments are examples of the presently disclosed techniques. Additionally, in an effort to provide a concise description of these embodiments, features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Acquisition and analysis of representative formation fluid samples downhole is useful for determining the economic value of hydrocarbon reserves and oil field development. However, formation fluid samples may be contaminated with drilling fluids that invade the geological formation during and/or after drilling operations. As such, it may be difficult to assess a composition of the geological formation fluid (also referred to as "native formation fluid") and determine the economic value of the hydrocarbon reserves. For example, native formation fluids, such as gas, oil, and formation water, may be miscible with the drilling fluid (e.g., oil-based mud filtrate or water-based mud filtrate), thereby affecting sample quality and analysis. Downhole acquisition tools may acquire formation fluid (e.g., drilling mud contaminated formation fluid or uncontaminated formation fluid/native formation fluid) and test the formation fluid to determine and/or estimate an amount of mud filtrate in the formation fluid. Based on the amount of mud filtrate in the formation fluid, an operator of the downhole acquisition tool may determine when the formation fluid sample is representative of the native reservoir fluid. In this way, the fluid properties and composition of the native reservoir fluid may be analyzed to determine the economic value of the hydrocarbon reserve. In addition, monitoring mud contamination downhole, e.g., in real time, avoids delays associated with fluid analysis at surface or at a remote location (e.g., offsite laboratory), thereby enabling real-time decision making at the well site and decreasing the overall operational costs of wellbore drilling operations.

Certain downhole acquisition tools may include multiple probes that flow the formation fluid through the tool for analysis. For example, in focused sampling applications, the downhole acquisition tool includes a sampling probe and a guard probe. The multi-probe configuration of the downhole acquisition tool may facilitate separation of contaminants (e.g., mud filtrate, mud filter cake) from the native formation fluid, and allow collection of a representative sample of the native formation fluid (e.g., uncontaminated formation fluid) for analysis in a faster amount of time compared to single probe downhole acquisition tools. The guard probe may have a faster flow rate compared to the sampling probe such that the guard probe draws the mud filtrate away from the sampling probe. Once the formation fluid sample in the sampling probe is representative of the native reservoir fluid, the sampling probe may fill sample bottles to collect the formation fluid sample. The filled sample bottles may be taken to surface and further analysis of the native reservoir fluid may be performed. However, filling the sample bottles with the formation fluid may take an undesirable amount of time due to the slow flow rate of the sampling probe used to obtain a flow rate ratio between the sampling probe and the guard probe that may maintain the amount of mud filtrate contamination in the sample of the formation fluid at or below the desired contamination level. Therefore, the sample bottle filling time may be undesirably long, which may drive up rig times and the overall cost of exploration and drilling operations.

The systems and methods of this disclosure may decrease the sample bottle filling times while also maintaining contamination levels within the formation fluid sample below a desired threshold, which may enable operators to reduce rig times and operational costs associated with the downhole fluid analysis. Accordingly, present embodiments include techniques that control the flow rate of the formation fluid through the sampling probe the downhole acquisition tool based on a relationship between the contamination level of the formation fluid sample flowing through the sampling probe and the flow rate of the guard probe. This may decrease the amount of time it takes to fill the sample bottles with the formation fluid sample.

Figure 2:
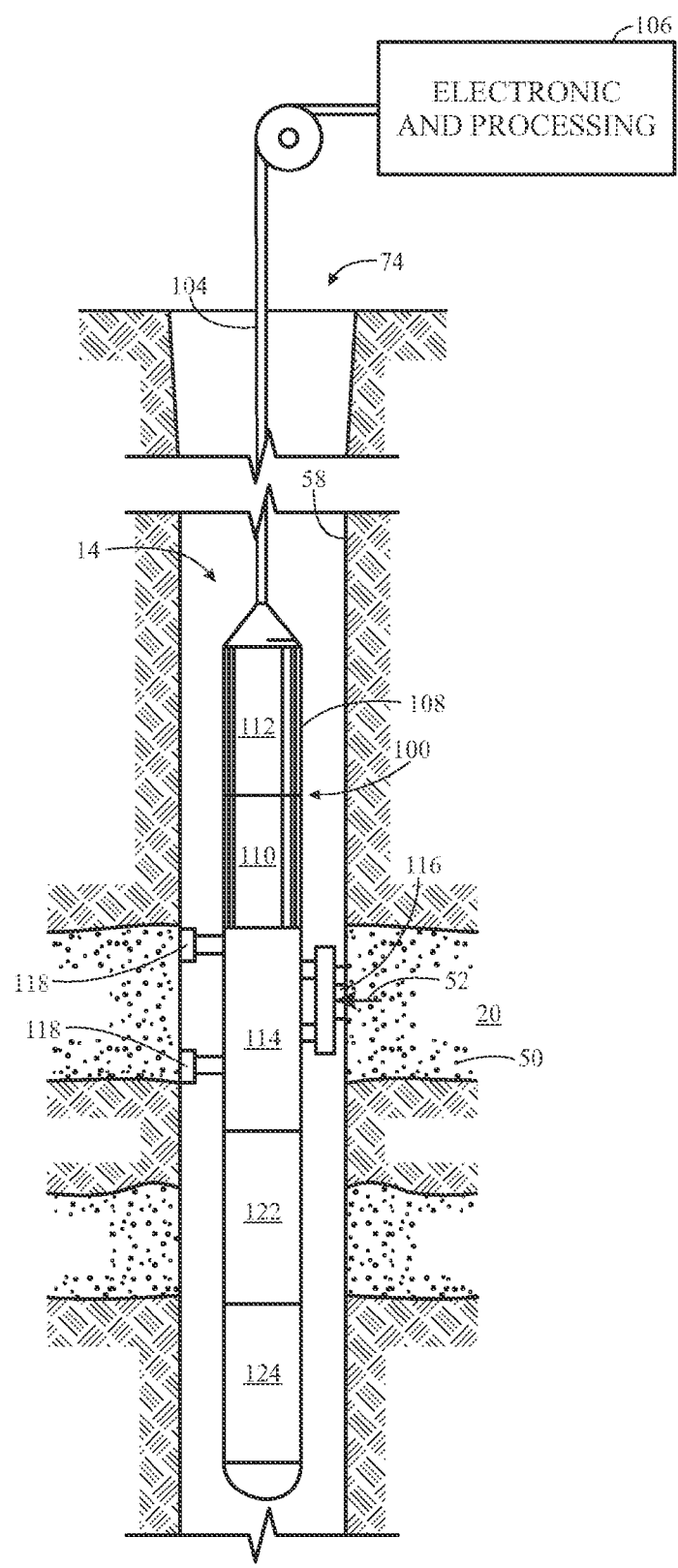
FIG. 2 is a schematic diagram of another embodiment of a wellsite system that may employ downhole fluid analysis methods for determining mud contamination in a formation fluid, in accordance with an embodiment.

FIGS. 1 and 2 depict examples of wellsite systems that may employ the fluid analysis systems and techniques described herein. FIG. 1 depicts a rig 10 with a downhole acquisition tool 12 suspended therefrom and into a wellbore 14 via a drill string 16. The downhole acquisition tool 12 has a drill bit 18 at its lower end thereof that is used to advance the downhole acquisition tool 12 into a geological formation 20 and form the wellbore 14. The drill string 16 is rotated by a rotary table 24, energized by means not shown, which engages a kelly 26 at the upper end of the drill string 16. The drill string 16 is suspended from a hook 28, attached to a traveling block (also not shown), through the kelly 26 and a rotary swivel 30 that permits rotation of the drill string 16 relative to the hook 28. The rig 10 is depicted as a land-based platform and derrick assembly used to form the wellbore 14 by rotary drilling. However, in other embodiments, the rig 10 may be an offshore platform.

Drilling fluid or mud 32 (e.g., oil-based mud (OBM) or water-base mud (WBM)) is stored in a pit 34 formed at the well site. A pump 36 delivers the drilling fluid 32 to the interior of the drill string 16 via a port in the swivel 30, inducing the drilling mud 32 to flow downwardly through the drill string 16 as indicated by a directional arrow 38. The drilling fluid exits the drill string 16 via ports in the drill bit 18, and then circulates upwardly through the region between the outside of the drill string 16 and the wall of the wellbore 14, called the annulus, as indicated by directional arrows 40. The drilling mud 32 lubricates the drill bit 18 and carries formation cuttings up to the surface as it is returned to the pit 34 for recirculation.

The downhole acquisition tool 12, sometimes referred to as a bottom hole assembly ("BHA"), may be positioned near the drill bit 18 and includes various components with capabilities, such as measuring, processing, and storing information, as well as communicating with the surface. A telemetry device (not shown) also may be provided for communicating with a surface unit (not shown). As should be noted, the downhole acquisition tool 12 may be conveyed on wired drill pipe, a combination of wired drill pipe and wireline, or other suitable types of conveyance.

The downhole acquisition tool 12 further includes a sampling system 42 including a fluid communication module 46, a sampling module 48, and a sample bottle module 49. The modules may be housed in a drill collar for performing various formation evaluation functions, such as pressure testing and fluid sampling, among others and collecting representative samples of native formation fluid 50. As shown in FIG. 1, the fluid communication module 46 is positioned adjacent the sampling module 48; however the position of the fluid communication module 46, as well as other modules, may vary in other embodiments. Additional devices, such as pumps, gauges, sensors, monitors or other devices usable in downhole sampling and/or testing also may be provided. The additional devices may be incorporated into modules 46, 48 or disposed within separate modules included within the sampling system 42.

In certain embodiments, the downhole acquisition tool 12 may evaluate fluid properties of the drilling mud 32, the native formation fluid 50, and/or a contaminated formation fluid, as illustrated by arrow 52. Accordingly, the sampling system 42 may include sensors that may measure fluid properties such as gas-to-oil ratio (GOR); mass density; optical density (OD); composition of carbon dioxide ($CO_2$), $C_1$, $C_2$, $C_3$, $C_4$, $C_5$, and/or $C_{6+}$; formation volume factor; viscosity; resistivity; conductivity, fluorescence; compressibility, and/or combinations of these properties of the drilling mud 32, the native formation fluid 50 (e.g., native formation water or hydrocarbons), and/or formation fluid 52. As should be noted, the formation fluid 52 may be the drilling mud 32, the native formation fluid 50, or a mixture of the drilling mud 32 and the native formation fluid 50. For example, during drilling, the drilling mud 32 may penetrate wellbore wall 58, as illustrated by arrow 54, thereby contaminating the native formation fluid 50. Therefore, as discussed in further detail below, the sampling system 42 may be used to monitor mud filtrate contamination to determine an amount of the drilling mud filtrate 54 in the formation fluid 52 (e.g., the drilling mud 32, the native formation fluid 50, or a combination thereof).

The fluid communication module 46 includes a probe 60, which may be positioned in a stabilizer blade or rib 62. The probe 60 includes one or more inlets for receiving the formation fluid 52 and one or more flow lines (not shown) extending into the downhole tool 12 for passing fluids (e.g., the formation fluid 52) through the tool. In certain embodiments, the probe 60 may include a single inlet designed to direct the formation fluid 52 into a flowline within the downhole acquisition tool 12. Further, in other embodiments, the probe 60 may include multiple inlets (e.g., a sampling probe and a guard probe) that may, for example, be used for focused sampling. In these embodiments, the probe 60 may be connected to a sampling flow line, as well as to guard flow lines. The probe 60 may be movable between extended and retracted positions for selectively engaging the wellbore wall 58 of the wellbore 14 and acquiring fluid samples from the geological formation 20. One or more setting pistons 64 may be provided to assist in positioning the fluid communication device against the wellbore wall 58.

The sensors within the sampling system 42 may collect and transmit data 70 associated with the fluid properties and the composition of the formation fluid 52 to a control and data acquisition system 72 at surface 74, where the data 70 may be stored and processed in a data processing system 76 of the control and data acquisition system 72.

The data processing system 76 may include a processor 78, memory 80, storage 82, and/or display 84. The memory 80 may include one or more tangible, non-transitory, machine readable media collectively storing one or more sets of instructions for operating the downhole acquisition tool 16 and estimating an amount of mud filtrate 54 (e.g., drilling mud 32) in the formation fluid 52. The memory 80 may store mixing rules and algorithms associated with the native formation fluid 50 (e.g., uncontaminated formation fluid), the drilling mud 32, and combinations thereof to facilitate estimating an amount of the drilling mud 32 in the formation fluid 52. The data processing system 76 may use the fluid property and composition information of the data 70 to estimate an amount of the mud filtrate in the formation fluid 52 and adjust a flow rate of flowlines associated with the probe 60. For example, the memory 80 may store one or more algorithms that use the estimate of the amount of the mud filtrate 54 and the flow rate of the formation fluid in the guard flowline to adjust the flow rate of the sampling probe, as discussed in further detail below with reference to FIGS. 3-11.

In certain embodiments, the data processing system 76 may apply filters to remove noise from the data 70. In addition, the data processing system 76 may select fluid property data 70 that has enough contrast between the native formation fluid 50 and the pure mud 32. For example, certain fluid and compositional parameters between the native formation fluid 50 and the pure mud filtrate 54 (e.g., the drilling mud 32) may be similar, such that it may be difficult to differentiate between the two fluids. However, by selecting parameters that clearly differentiate the native formation fluid 50 and the pure mud filtrate 54, the quantification accuracy of the mud filtrate 54 contamination may be increased. By way of example, the data processing system 76 may select fluid property parameters such as optical density (OD), density, resistivity, and conductivity, f-function (e.g., gas-to-oil ratio), compressibility, among others to determine the amount of mud filtrate 54 contamination in the native formation fluid 50.

To process the data 70, the processor 78 may execute instructions stored in the memory 80 and/or storage 82. For example, the instructions may cause the processor to quantify the amount of mud filtrate 54 contamination in the formation fluid 52, estimate fluid and compositional parameters of the native formation fluid 50 and the pure mud filtrate 54, and control flow rates of the sample and guard probes, as discussed in further detail below. As such, the memory 80 and/or storage 82 of the data processing system 76 may be any suitable article of manufacture that can store the instructions. By way of example, the memory 80 and/or the storage 82 may be ROM memory, random-access memory (RAM), flash memory, an optical storage medium, or a hard disk drive. The display 84 may be any suitable electronic display that can display information (e.g., logs, tables, cross-plots, etc.) relating to properties of the well as measured by the downhole acquisition tool 16. It should be appreciated that, although the data processing system 76 is shown by way of example as being located at the surface 74, the data processing system 76 may be located in the downhole acquisition tool 16. In such embodiments, some of the data 70 may be processed and stored downhole (e.g., within the wellbore 14), while some of the data 70 may be sent to the surface 74 (e.g., in real time).

FIG. 2 depicts an example of a wireline downhole tool 100 that may employ the systems and techniques described herein to monitor mud contamination of the formation fluid 52 and control the flow rates of the sampling and guard probes. The downhole tool 100 is suspended in the wellbore 14 from the lower end of a multi-conductor cable 104 that is spooled on a winch at the surface 74. Similar to the downhole acquisition tool 12, the wireline downhole tool 100 may be conveyed on wired drill pipe, a combination of wired drill pipe and wireline, or other suitable types of conveyance. The cable 104 is communicatively coupled to an electronics and processing system 106. The downhole tool 100 includes an elongated body 108 that houses modules 110, 112, 114, 122, and 124, that provide various functionalities including fluid sampling, sample bottle filling, fluid testing, operational control, and communication, among others. For example, the modules 110 and 112 may provide additional functionality such as fluid analysis, resistivity measurements, operational control, communications, coring, and/or imaging, among others.

As shown in FIG. 2, the module 114 is a fluid communication module 114 that has a selectively extendable probe 116 and backup pistons 118 that are arranged on opposite sides of the elongated body 108. The extendable probe 116 is configured to selectively seal off or isolate selected portions of the wall 58 of the wellbore 14 to fluidly couple to the adjacent geological formation 20 and/or to draw fluid samples from the geological formation 20. The probe 116 may include a single inlet or multiple inlets designed for guarded or focused sampling. The native formation fluid 50 may be expelled to the wellbore through a port in the body 108 or the formation fluid 52, including the native formation fluid 50, may be sent to one or more fluid sampling modules 122 and 124. The fluid sampling modules 122 and 124 may include sample chambers that store the formation fluid 52. In the illustrated example, the electronics and processing system 106 and/or a downhole control system are configured to control the extendable probe assembly 116 and/or the drawing of a fluid sample from the geological formation 20 to enable analysis of the formation fluid 52 for oil based mud filtrate contamination, as discussed above.

Figure 3:
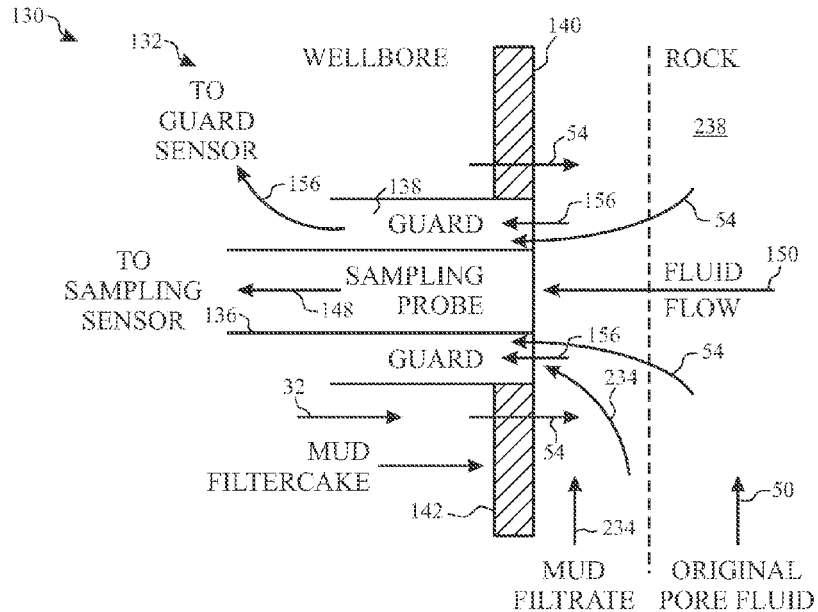
FIG. 3 depicts a geometrical model of a focused sampling tool, in accordance with one or more embodiments of the present disclosure.

FIG. 3 illustrates an embodiment of a geometrical model 130 of the downhole acquisition tool 12 that uses focused sampling for downhole fluid analysis applications. In the model 130, the downhole acquisition tool 12 includes a multi-intake probe 132 that includes a sampling probe 136 and a guard probe 138 surrounding the sampling probe 136. As discussed above, the mud filtrate 54 (e.g., the oil-based or water-based mud) may penetrate the formation, thereby contaminating the native formation fluid 50. For example, in the illustrated embodiment, drilling mud 32 penetrates formation wall 140. A portion of the drilling mud 32 (e.g., suspended solids) may form a mud filter cake 142 against the formation wall 140 as the mud filtrate 54 flows through the formation wall 140. The mud filtrate 54 may mix with native formation fluid 50 (e.g., uncontaminated formation fluid) within formation 20 (e.g., rock), thereby contaminating the native formation fluid 50.

In focused sampling, the guard probe 138 may separate a portion of the mud filtrate 54 from the native formation fluid 50 during sampling. For example, as illustrated in FIG. 3, a first fraction 148 of a total flow of formation fluid 150 (e.g., the mud filter cake 142, the mud filtrate 54, and the native formation fluid 50) enters the sampling probe 136, and a second fraction 156 of the total formation fluid 150 enters the guard probe 138. A pump associated with the guard probe 138 may operate at a higher speed compared to a sample probe pump to allow a larger drawdown and higher flow rate of the second fraction 156 compared to the first fraction 148. As such, mud filtrate clean-up time in the sample probe 136 may be decreased compared to downhole acquisition tools that do not use focused sampling for downhole fluid analysis. Therefore, the first fraction 148 may have a lower amount of mud contamination (e.g., the mud filtrate 54) compared to the second fraction 156.

Once the operator of the downhole acquisition tool 12 determines, based on the fluid property measurements from the downhole acquisition tool 12, that the first fraction 148 in the sampling probe 136 has a contamination level below a desired threshold (e.g., less than or equal to 1% contamination), the first fraction 148 is collected in sample bottles. The first fraction 148 collected in the sample bottle may be a representative sample of the native formation fluid 50. The higher drawdown and flow rate of the second fraction 156 through the guard probe 138 compared to the first fraction 148 through the sampling probe 136 may facilitate maintaining contamination levels in the first fraction 148 at or below the desired threshold by drawing a portion of the first fraction 148 away from the sampling probe 136. This allows the contaminants to continue flowing through the guard probe 138 rather than the sampling probe 136 once the sampling probe 136 reaches the desired clean-up contamination level.

However, due, in part, to the lower pump speed and flow rate of the sampling probe 136 compared to the guard probe 136, the sample bottle may take an undesirable amount of time to fill up with the first fraction 148. This may cause undesirable sample bottle filling times, which may result in longer rig times and increase the operational costs of downhole fluid analysis operations. As discussed in further detail below, gradually and continuously increasing the flow rate of the first fraction 148 though the sampling probe 136 once the contamination level of the first fraction 148 is at or below a desired threshold as measured by the downhole acquisition tool 12 may decrease sample bottle filling times while maintaining the contamination level of the first fraction 148 at or below the desired threshold during bottle filling. In certain embodiments, the flow rate of the first fraction 148 through the sample probe 136 may be adjusted based on a relationship between the contamination level of the fractions 148, 156 and a flow rate ratio between a sampling probe and a guard probe.

Figure 4:
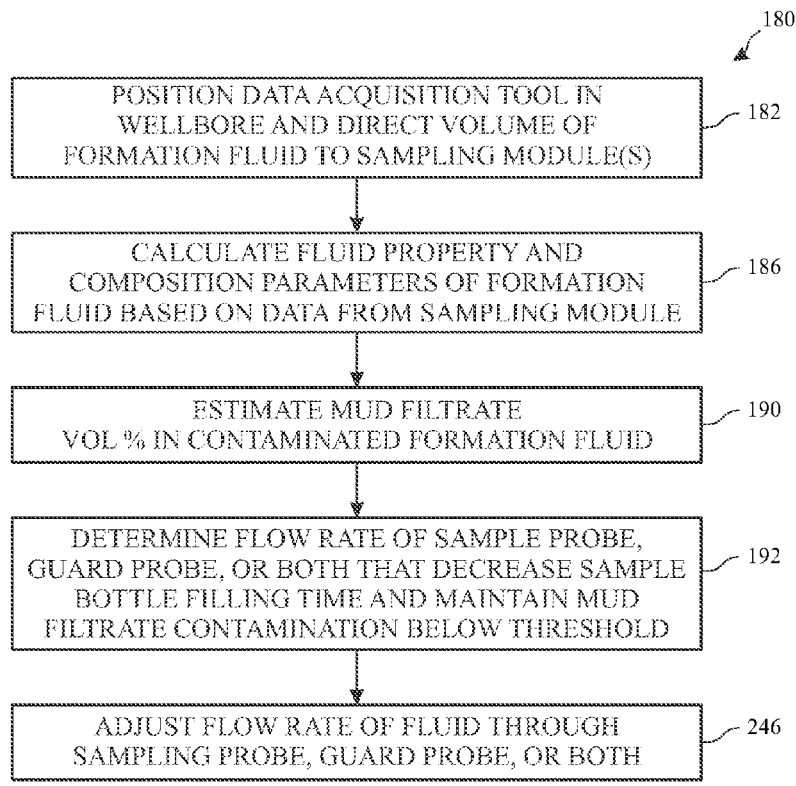
FIG. 4 is a flowchart depicting a method of adjusting a flow rate of a fluid through a probe of the downhole acquisition tool of FIGS. 1 and 2, in accordance with one or more embodiments of the present disclosure.

FIG. 4 illustrates a flowchart 180 of a method for monitoring the contamination level in the formation fluid 52 using the downhole acquisition tool 12. To facilitate the following discussion, reference will be made to the downhole acquisition tool 12. However, the embodiments disclosed herein may also be done using the wireline downhole tool 100. In accordance with the illustrated flowchart 180, the downhole acquisition tool 12 is positioned at a desired depth within the wellbore and a volume of the formation fluid 52 is directed to the sampling modules (e.g., modules 20, 22, 24) for analysis (block 182). For example, the downhole acquisition tool 12 is lowered into the wellbore, as discussed above with reference to FIGS. 1 and 2, such that the probe module 42 is within a fluid sampling region of interest. The probe module 42 faces toward the geological formation to enable a flow of the formation fluid 52 through each flowline of the respective probes 136, 138 through the respective flowline toward the sampling modules 48, 122, 124.

While in the downhole acquisition tool 12, the multiple sensors detect and transmit fluid and compositional parameters (e.g., the data 70) of the formation fluid 52 such as, but not limited to, resistivity, conductivity, density (p), composition, optical density (OD), shrinkage factor (b), pH, gas-to-oil ratio (GOR), compressibility, and any other suitable parameter of the formation fluid 52 to the data processing system 76. The data processing system 76 applies one or more algorithms to calculate the fluid property of the formation fluid 52 based on the data from the modules 48, 122, 124 (block 186). For example, the data processing system 76 may calculate the fluid parameters based on mixing rule algorithms derived for binary fluids, such as oil-based mud (OBM) contaminated formation fluid.

Once the fluid property data for the formation fluid is measured, the data processing system 76 may estimate endpoint values for the native formation fluid 50 and the pure mud filtrate 52, and the mud filtrate contamination level may be determined. For example, power functions (e.g., exponential, asymptote, or other functions) may be used to fit the data (e.g., real time data) from the downhole fluid analysis to determine the fluid properties of the native formation fluid 50. Derivation of a power-law decay model is described in U.S. Patent Application Ser. No. 61/985,376 assigned to Schlumberger Technology Corporation and is hereby incorporated by reference in its entirety. By way of example, power-law models that may be used for obtaining native formation fluid 50 and pure mud filtrate 54 fluid properties are expressed as:

$$v_{mf} = \frac{OD_{0i} - OD_i}{OD_{0i} - OD_{mfl}} = \frac{f_o - f}{f_o - f_{mf}} = \frac{b_o - b}{b_o - b_{mf}} = \frac{\rho_o - \rho}{\rho_o - \rho_{mf}} = \frac{q_{oj} - q_j}{q_{oj} - q_{mfj}} = \beta V(t)^{-\gamma} \quad (EQ.\ 1)$$

where
$v_{mf}$ is the contamination level of the native formation fluid 50
V(t) is the volume of fluid pumped from the geological formation to the drilling fluid analysis at time t
$\gamma$ is a parameter of the probe sampling
$\beta$ is an adjustable parameter
subscripts 0, mf, i, and j represent the uncontaminated formation fluid (e.g., the native formation fluid 50), pure mud filtrate 54, optical channel i, and component j in the formation fluid 52, respectively.

$$FP = a + bV(t)^{-\gamma} \quad (EQ.\ 2)$$

where
FP is the selected fluid property (e.g., optical density, density, composition, etc.) of the formation fluid
a and b are adjustable fitting parameter Once the fluid property and compositional parameters of the native formation fluid 50 and the pure mud (e.g., the drilling mud 32/mud filtrate 54) have been established, as discussed above, the amount (e.g., % volume) of the mud filtrate 54 in the formation fluid 52 may be estimated (block 190). Over time (or formation fluid pump-out volume) the amount of mud filtrate contamination in the fractions 148, 156 decreases as a total amount of the mud filtrate 54 surrounding the sampling system 42 of the downhole acquisition tool 12 decreases. Due, in part, to the higher drawdown and flow rate of the second fraction 156 through the guard probe 138, the sampling probe 136 may achieve clean-up before the guard probe 138. The data processing system 76 may calculate a total flow rate weighted average contamination $\eta_{tot}$ of the formation fluid 50 (e.g., the fractions 148, 156) and a total flow rate $Q_{tot}$ of the downhole acquisition tool 12, respectively, over time using EQs. 3 and 4, respectively, to determine when the desired contamination level threshold is reached in the sampling probe 136.

$$\eta_{tot}(t) = \frac{Q_s(t)\eta_s(t) + Q_g(t)\eta_g(t)}{Q_s(t) + Q_g(t)} \quad \text{(EQ. 3)}$$

where
$\eta_s$ is the contamination level in sample flowline
$\eta_g$ is the contamination level in the guard flowline
$Q_s$ is the flow rate through the sampling probe
$Q_g$ is the flow rate through the guard probe
t is time $$Q_{tot}(t) = Q_s(t) + Q_g(t) \quad \text{(EQ. 4)}$$

The downhole acquisition tool 16 may begin to collect the first fraction 148 and fill the sample bottles when the amount of the mud filtrate 54 in the first fraction 148 is at or below the desired contamination level threshold. In certain embodiments, the contamination level threshold may be between approximately 1% and approximately 2% mud filtrate contamination in the first fraction 148. However, as shown in EQ. 3, the contamination levels in formation fluid 52 (e.g., $\eta_{tot}$) and the fractions 148, 156 (e.g., $\eta_s$, $\eta_g$) at any given time during pumping of the formation fluid 52 through the downhole acquisition tool 12 are dependent on the flow rates associated with the sampling probe 136 and the guard probe 138. Therefore, changing the flow rates of the fraction 148, 156 through the respective probe 136, 138 to decrease sample bottle filling times may also change the contamination levels of the first fraction 148 (e.g., $\eta_s$), the second fraction 156 (e.g., $\eta_g$), or both. As such, the formation fluid sample collected in the sample bottles may have an undesirable amount of mud filtrate contamination, and the formation fluid sample may not be representative of the native formation fluid 50.

Accordingly, the method 180 includes determining a flow rate of the sampling probe, the guarding probe, or both that maintains the contamination level in the first fraction 148 at or below the contamination level threshold (block 192), while decreasing sample bottle filling times. For example, the data processing system 76 may determine the sample flow rate $Q_s$, the guard flow rate $Q_g$, sample flowline contamination $\eta_s$, and guard flowline contamination $\eta_g$ as a function of time. The flow rates $Q_s$ and $Q_g$ may be determined based on the speed of the pumps associated with the respective probes 136, 138. The sample and guard flowline contamination $\eta_s$ and $\eta_g$, respectively, may be determined by fitting and extrapolating a power-law decay model such as the power-law decay models expressed in EQ. 1 and 2.

For example, the power-law model in EQ. 2 may be fit to the available total flow rate weighted average contamination level $\eta_{tot}(t)$ data, which is the cumulative contamination data available up to a time t from the start of the downhole fluid analysis. The model data fit to the available $\eta_{tot}(t)$ data may be extrapolated to predict the total weighted average contamination level at any time after time t (e.g., $\eta_{tot}(t+\Delta t)$). However, as shown in EQ. 2, $\eta_{tot}(t)$ is dependent on the sample and guard flowline contamination levels $\eta_s(t)$ and $\eta_g(t)$, respectively. Accordingly, the data processing system 76 may need to estimate the flowline contamination levels $\eta_s(t)$ and $\eta_g(t)$ to determine $\eta_{tot}(t)$ before the power-decay model fitting and extrapolation.

The data processing system 76 may estimate the sample and guard flowline contamination levels $\eta_s(t)$ and $\eta_g(t)$, respectively, based on the fluid properties (e.g., optical density (OD), density, gas-to-oil ratio, compressibility, composition among others) of the formation fluid 50 as measured by the downhole acquisition tool 12. In certain embodiments, the data processing system 76 may use a liner relationship between the fluid property of the formation fluid 50 and the contamination level of the formation fluid 50 in the sampling probe 136, the guard probe 138, or both. By way of example, fluid properties such as, but not limited to, optical density (OD), density, f-function (e.g, gas-to-oil ratio), composition, resistivity, formation volume factor (FVF), compressibility, or any other suitable fluid property may be used to determine the contamination level of the formation fluid 52. However, in downhole fluid analysis, the fluid properties of the native reservoir fluid 50 and the pure mud filtrate 52 are generally unknown. Therefore, end point values (e.g., fluid properties of the native reservoir fluid 50 and the pure mud filtrate 54) may be estimated by the power-law decay model fitting and extrapolation, as discussed above. To facilitate discussion of the present embodiments, the following discussion is in the context of using the OD of the formation fluid 52 to determine the sampling and guard flowline contamination levels. However, any other fluid property of the formation fluid 52 may be used.

Based on Beer Lambert's law, a linear relationship exists between the optical density (OD) and the contamination level of the formation fluid 52. Due, in part, to this linear relationship, EQ. 5 may be derived from EQ. 3.

$$OD_{tot}(t) = \frac{Q_s(t)OD_s(t) + Q_g(t)OD_g(t)}{Q_s(t) + Q_g} \quad \text{(EQ. 5)}$$

where $OD_{tot}(t)$ is the total flow rate weighted optical density derived from sample and guard OD measurements and the respective flow rates associated with the probes 136, 138 up to the time t. The power-law decay models in EQs. 1 and 2 may be fitted to the OD data determined from EQ. 5 (or to $OD_s(t)$), and extrapolated to estimate an OD end point value of the formation fluid 52. Once the end point value of the native formation fluid 50 and/or the pure mud filtrate 54 are known, the flowline contamination levels $\eta_s$, $\eta_g$ and the flow rate weighted average contamination $\eta_{tot}$ in the fractions 148, 156 may be determined.

As discussed above, other fluid properties of the formation fluid 52 may also be used such as conductivity, density, formation volume factor, compressibility, resistivity, composition, and f-function (gas-to-oil ratio) among others. For example similar to the OD, density $\rho$ also has a linear relationship with mud filtrate contamination. Therefore, a relationship between the density $\rho$ and the sample and guard flow rates $Q_s$ and $Q_g$, respectively, may be expressed as follows:

$$\rho_{tot}(t) = \frac{Q_s(t)\rho_s(t) + Q_g(t)\rho_g(t)}{Q_s(t) + Q_g(t)} \quad \text{(EQ. 6)}$$

Following determination of the flowline contamination $\eta_s$, $\eta_g$, and flow rate weighted average contamination $\eta_{tot}$, the data processing system 76 may determine the sample and guard flow rate ratio that may be used to decrease the amount of sample bottle filling time while maintaining the sample flowline contamination level $\eta_s$ at or below the preset contamination level threshold, according to the acts of block 192. For example, the earliest time ($T_d$) that the first fraction 148 may reach the desired threshold contamination level may be denoted by the following relationship:

$$\eta_s(T_d) \leq \eta_{sd} \quad \text{(EQ. 7)}$$

where $\eta_{sd}$ is a preset contamination level threshold of the first fraction 148.

Therefore, to maintain a fixed contamination level (e.g., $\leq \eta_{sd}$) of the first fraction 148 in the sampling probe 136 at time (t) or (t+$\Delta$t) greater than $T_d$, EQ. 3 may be rewritten as follows:

$$Q_g(t) = \frac{\eta_{tot}(t) - \eta_{sd}}{\eta_g(t) - \eta_{sd}} Q_{tot}(t) \quad \text{(EQ. 8)}$$

$$Q_g(t+\Delta t) = \frac{\eta_{tot}(t+\Delta t) - \eta_{sd}}{\eta_g(t+\Delta t) - \eta_{sd}} Q_{tot}(t+\Delta t) \quad \text{(EQ. 9)}$$

The guard flow rate may be calculated by taking a ratio of EQ. 8 and EQ. 9, as shown below in EQ. 10. The calculated guard flow rate $Q_g$ may be used to determine the sample flow rate $Q_s$ by using EQ. 4. By using the preset contamination level threshold $\eta_{sd}$ to determine the sample and guard flow rates, a ratio of the sample and guard flow rates $Q_s$ and $Q_g$, respectively, at time t and t+$\Delta$t is such that the sample flowline contamination level $\eta_s$ remains at or below the preset contamination level threshold $\eta_{sd}$ during sample bottle filling.

$$Q_g(t+\Delta t) = \quad \text{(EQ. 10)}$$
$$\left(\frac{\eta_{tot}(t+\Delta t) - \eta_{sd}}{\eta_g(t+\Delta t) - \eta_{sd}}\right)\left(\frac{\eta_g(t) - \eta_{sd}}{\eta_{tot}(t) - \eta_{sd}}\right)\left(\frac{Q_{tot}(t+\Delta t)}{Q_{tot}(t)}\right) Q_g(t)$$

In certain embodiments, the first term on the right side of EQ. 10 may be less than 1. For example, over time the total flow rate weighted average contamination $\eta_{tot}$ of the formation fluid 52 may decrease (e.g., as the pump-out volume of the formation fluid 52 increases). As such, the $\eta_{tot}$(t+$\Delta$t) may be less than $\eta_{tot}$(t). However, the actual value of the first term on the right of EQ. 10 may still be unknown. Therefore, due, in part, to the relationship between the sample and guard flow rates $Q_s$ and $Q_g$, respectively, the sample and guard flow rates $Q_s$ and $Q_g$ may be set at time t+$\Delta$t such that the sample flowline contamination level $\eta_s$ remains below the preset contamination level threshold $\eta_{sd}$ during sample bottle filling, but the total flow rate weighted average contamination $\eta_{tot}$ and the guard probe contamination $\eta_g$ that result from a change in the sample flow rate $Q_s$ applied to the sampling probe 136 at the time t+$\Delta$t may remain unknown. Therefore, the first term on the right of EQ. 10 may be set as a as shown below in EQ. 11. Setting the first term on the right of EQ. 10 as a may allow the guard flowline contamination level $\eta_g$ at the subsequent t+$\Delta$t time point to be expressed as shown in EQ. 12 while maintaining the sample flowline contamination level $\eta_s$ at the subsequent t+$\Delta$t time point at the contamination level threshold $\eta_{sd}$.

$$\alpha = \frac{\eta_{tot}(t+\Delta t) - \eta_{sd}}{\eta_g(t+\Delta t) - \eta_{sd}} \leq 1 \quad \text{(EQ. 11)}$$

$$\eta_g(t+\Delta t) = \frac{1}{\alpha}\eta_{tot}(t+\Delta t) - \frac{1-\alpha}{\alpha}\eta_{sd} \quad \text{(EQ. 12)}$$

Accordingly, the guard flowline contamination level $\eta_g$ over time may be constrained as follows:

$$0 \leq \eta_g(t+\Delta t) \leq 1 \quad \text{(EQ. 13)}$$

Therefore, based on the constraints defined in EQ. 13, $\alpha$ is constrained as follows:

$$\frac{\eta_{tot}(t+\Delta t) - \eta_{sd}}{1 - \eta_{sd}} \leq \alpha \quad \text{(EQ. 14)}$$

Combining the constraints defined in EQs. 13 and 14, a general constraint of $\alpha$ may be written as:

$$\max\left(0, \frac{\eta_{tot}(t-\Delta t) - \eta_{sd}}{1 - \eta_{sd}}\right) \leq \alpha \leq 1 \quad \text{(EQ. 15)}$$

Moreover, to set a may allow the data processing system 76 to set the guard flow rate $Q_g$ at t+$\Delta$t such that the guard flowline contamination $\eta_g$ remains constant for t>$T_d$ and the total flow rate remains constant for t>$T_d$ as expressed in the following relationships:

$$\eta_g(t+\Delta t) = \eta_g(t) = \eta_g(T_d) \quad \text{(EQ. 16)}$$

$$Q_{tot}(t) = Q_{tot}(T_d) \quad \text{(EQ. 17)}$$

Accordingly, EQ. 16 may be rewritten as shown in EQ. 18 to select the value of $\alpha$:

$$\alpha = \frac{\eta_{tot}(t) - \eta_{sd}}{\eta_g(T_d) - \eta_{sd}} \quad \text{(EQ. 18)}$$

Applying EQ. 18 to select a, the sample and guard contamination levels may be kept constant by gradually decreasing the guard flow rate $Q_g$ and increasing the sample flow rate $Q_s$ as the total contamination level of the formation fluid 52 flowing through the downhole acquisition tool 12 (e.g., the fractions 148, 156) decreases. Therefore, EQ. 10 may be simplified by using the relationships expressed in EQs. 16 and 17 as follows:

$$Q_g(t+\Delta t) = \frac{\eta_g(t) - \eta_{sd}}{\eta_g(T_d) - \eta_{sd}} Q_g(t) \quad \text{(EQ. 19)}$$

In certain embodiments, an efficiency factor $\beta$ may be applied to EQ. 19 to correct for changes in guarding efficiency (e.g., focusing) of the guard probe 138. For example, when the sample and guard flow rates $Q_s$ and $Q_g$, respectively, change during downhole fluid analysis, pressure drawdown in the probes 136, 138 may also change. This change may decrease the guarding efficiency of the guard probe 138. A decrease in the guarding efficiency may be shown as an increase in a desired fraction of the native formation fluid 50 in the total flow with which approximately 99% of the first fraction 148 flowing through the sampling probe 136 may still be a representative sample of the native formation fluid 50. Therefore, EQ. 19 may be rewritten to include the efficiency factor β to correct for the changes in guarding efficiency resulting from the change in the flow rates of the probes 136, 138 as follows:

$$Q_g(t + \Delta t) = \frac{1}{\beta}\left(\frac{\eta_g(t) - \eta_{sd}}{\eta_g(T_d) - \eta_{sd}}\right)Q_g(t) \quad \text{(EQ. 20)}$$

The value of β may be determined based on simulations using simulation programs such as the Eclipse industry-reference reservoir simulator available from Schlumberger Technology Corporation or the Star CCM+® simulator available from CD-adapco. The simulations may provide information regarding to changes in clean-up flow rates resulting from drawdown ratio changes between the probes 136, 138. In certain embodiments, the value of β is greater than 0 and less than or equal to 1 (0≤β≤1).

In other embodiments, rather than keeping the total flow rate $Q_{tot}$ constant at time t>Td, it may be assumed that the total flow rate $Q_{tot}$ is kept constant at both times t and t+Δt. Additionally, the sample flowline contamination level $\eta_s$ may be assumed to be approximately equal to the preset contamination level threshold $\eta_{sd}$, and the guard flowline contamination level $\eta_g$ at time t+Δt may be equal to the guard flowline contamination level $\eta_g$ at $T_d$. Accordingly, EQ. 9 may be reduced as shown below in EQ. 21 by following the constraints in EQs. 22-24.

$$Q_g(t + \Delta t) = \left(\frac{\eta_{tot}(t + \Delta t) - \eta_{sd}}{\eta_g(T_d) - \eta_{sd}}\right)Q_{tot}(t) \quad \text{(EQ. 21)}$$

$$Q_{tot}(t + \Delta t) = Q_{tot}(t) \quad \text{(EQ. 22)}$$

$$\eta_s(t + \Delta t) = \eta_{sd} \quad \text{(EQ. 23)}$$

$$\eta_g(t + \Delta t) = \eta_g(T_d) \quad \text{(EQ. 24)}$$

As discussed above, the total flow rate weight average contamination level $\eta_{tot}$ may decrease over time. Therefore, EQ. 21 may be further reduced as expressed in EQ. 26 by setting the following constraint:

$$\eta_{tot}(t + \Delta t) < \eta_{tot}(t) \quad \text{(EQ. 25)}$$

$$Q_g(t + \Delta t) = \left(\frac{\eta_{tot}(t) - \eta_{sd}}{\eta_g(T_d) - \eta_{sd}}\right)Q_{tot}(t) \quad \text{(EQ. 26)}$$

Similar to EQ. 20, the efficiency factor β may also be applied to EQ. 26.

During the early phase of clean-up after the native formation fluid 50 break-through in the sampling probe 136, both probes 136, 138 may have similar drawdown of the fractions 148, 156, and the sample and guard flowline contamination levels $\eta_s$ and $\eta_g$, respectively, may follow a power-law decay model such as those expressed in EQs. 1 and 2. For example, the sample and guard flowline contamination $\eta_s$ and $\eta_g$, respectively, may follow a power-law decay model having n equal to −5/12. Therefore, the desired guard flowline contamination level $\eta_g$ may be expressed as follows:

$$\eta_g(t + \Delta t) = \eta_g(T_d) \cdot \left(\frac{t + \Delta t}{T_d}\right)^{-n} \quad \text{(EQ. 27)}$$

In this particular embodiment, $\eta_g(T_d)$ is the guard flowline contamination level at time $T_d$ when the sample flowline contamination level $\eta_s$ first reaches the contamination level threshold $\eta_{sd}$. Without rate optimization, the guard contamination is expected to behave proportionally with a $5/12^{th}$ power law. Therefore, the guard contamination target $\eta_g$ (t+Δt) may be determined according to EQ. 27. For example, selecting exponent v in EQ. 27 to be less than 5/12 for time t greater than $T_d$ may decrease the guard contamination level at a reduced rate relative to the relative constant guard line flow rates during the early phase clean-up, thereby resulting in an increase in the guard flow rate $Q_g$ over time in a predictable manner. Note that time t may be replaced by volume and $T_d$ may be replaced with $v_d$ (e.g., pumped volume of formation fluid when the contamination level threshold $\eta_{sd}$ is reached). Thus, in addition to the constraints set forth in EQs. 22 and 25, the following constraints may also be assumed:

$$\eta_g(t) \geq \eta_s(T_d) \quad \text{(EQ. 28)}$$

Based on the above constraints, EQ. 9 may be reduced as follows:

$$Q_g(t + \Delta t) = \left(\frac{\eta_{tot}(t) - \eta_{sd}}{\eta_{tot}\left(\frac{t + \Delta t}{T_d}\right)^{-n} - \eta_{sd}}\right)Q_{tot}(t) \quad \text{(EQ. 29)}$$

Similar to EQ. 20, the efficiency factor β may also be applied to EQ. 29. The guard flowline contamination level $\eta_g$(t+Δt) may be determined based on EQ. 27. When using EQ. 27 to determine the guard flowline contamination level $\eta_g$(t+Δt) term, a range of n-values are possible for the exponent n. The guard flowline contamination level $\eta_g$ at time t as determined based on EQ. 27 may be expected to behave with an n-value equal to 5/12 without flow rate optimization. However, the n-value may vary based on an inlet type associated with the probes 136, 138. Therefore, in certain embodiments, the n-values may be selected based on the inlet type of the probes 136, 138 of the downhole acquisition tool 12. If the n-value is selected to be too close to zero, the sample contamination level may increase above the preset contamination level threshold $r1_d$ due, in part, to changes in the guarding efficiency of the guard probe 138 that result from changes sample and guard flow rates and drawdown of the probes 136, 138. Therefore, n-value used in EQ. 27 may be constrained as follows:

$$0 < n < \frac{5}{12} \quad \text{(EQ. 30)}$$

Figure 5:
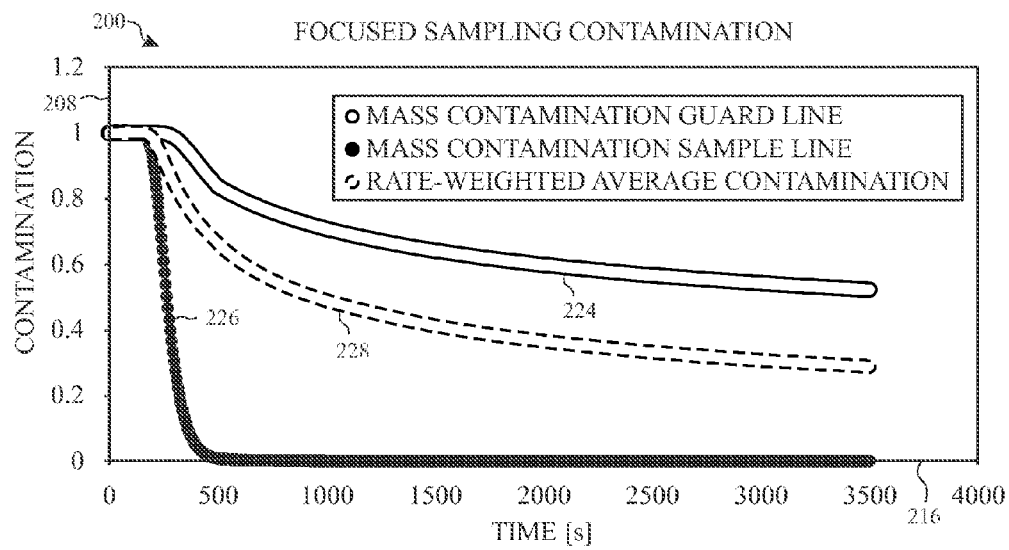
FIG. 5 depicts a graph reflecting a relationship between contamination of a first portion and a second portion of formation fluid as analyzed by a focused sampling tool and pump-out time, in accordance with one or more embodiments of the present disclosure.
Figure 6:
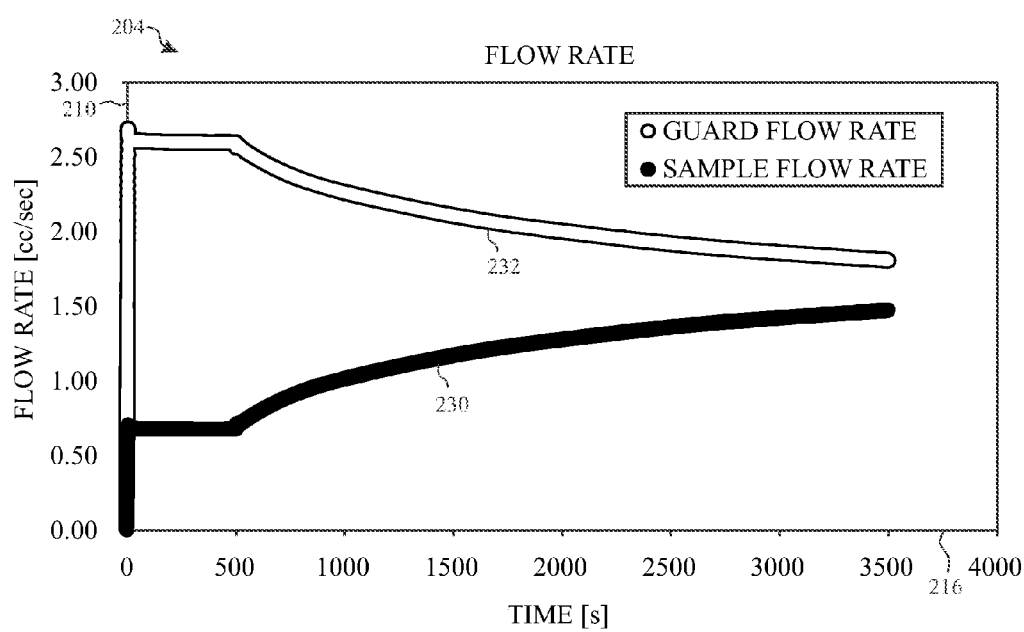
FIG. 6 depicts a graph reflecting a relationship between flow rates of the first portion and the second portion of the formation fluid as analyzed by the focused sampling tool over time, in accordance with one or more embodiments of the present disclosure.
Figure 7:
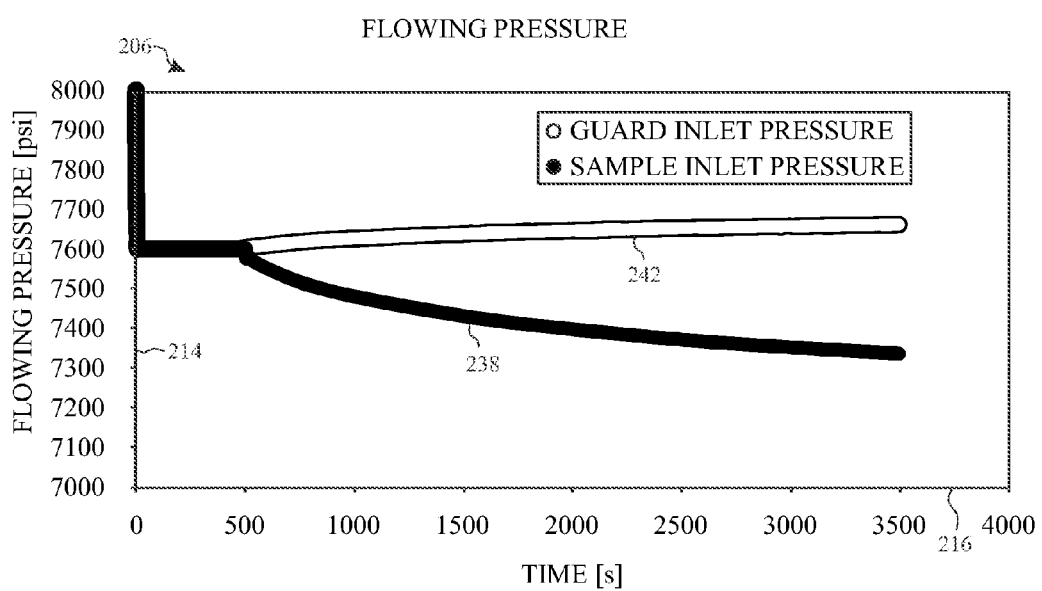
FIG. 7 depicts a graph reflecting a relationship between flowing pressure of a first probe inlet and a second probe inlet of the focused sampling tool over time, in accordance with one or more embodiments of the present disclosure.

FIGS. 5-7 are representative plots 200, 204, and 206 of contamination 208 (e.g., volumetric contamination), flow rate 210 in cubic centimeters (cc)/second (s), and flowing pressure 214 in pounds per square inch (psi), respectively, as a function of time 216 in seconds. The guard flow rate $Q_g$ was determined based on the guard flowline contamination level $\eta_g$ at time t determined using EQ. 27 with an n-value of 3/12 for the exponent n, and the preset contamination level threshold $\eta_{sd}$ at $T_d$ for the sample flowline contamination level $\eta_s$ was set at 0.01. As shown in plots 200 and 204, guard volume contamination 224, sample mass contamination 226, and total flow rate weighted average contamination 228 gradually decrease over time (FIG. 5) as sample flow rate 230 increases and guard sample flow rate 232 decreases over time 216 (FIG. 6) while maintaining the sample mass contamination 226 below the preset contamination level threshold $\eta_{sd}$ of 0.01. In this particular embodiment, the sample flowline contamination level $\eta_s$ reached the preset contamination level threshold $\eta_{sd}$ at approximately 500 seconds, as shown by the change in the sample and guard flow rates 230, 232, respectively, in FIG. 6.

FIG. 7 illustrates the change in sample inlet pressure 238 and guard inlet pressure 242 resulting from change in the sample and guard flow rates 230, 232, respectively. As shown in FIG. 7, the sample inlet pressure 238 decreases while the guard inlet pressure 242 increases as a result of the flow rate changes. As such, the drawdown in the guarding probe 138 is lower than the sampling probe 136. Such change in drawdowns may reduce the focusing efficiency resulting in the sampling probe 136 drawing in some mud filtrate 54 from the second fraction 156, which may increase the sample contamination level $\eta_s$ above the preset contamination level threshold $\eta_{sd}$. Choosing a less aggressive n-value such as 3/12 may compensate for the reduced focusing efficiency while still allowing the mud filtrate to continue to flow though the guard probe 138 at a guard flow rate $Q_g$ that is lower than the guard flow rate before the sample contamination level $\eta_s$ reached the preset contamination level threshold $\eta_{sd}$. As such, the sample flow rate 228 may be increased over time 216 compared to the sample flow rate 228 at the start of clean-up. In this way, the sample bottles may be filled at a desired amount of time without increasing the sample contamination 226 beyond the preset contamination level $\eta_{sd}$ once the sample mass contamination 226 is at or below the preset contamination level $\eta_{sd}$.

In embodiments, where $t>T_d$ and for elevated total contamination such as $\eta_{tot}(t)>0.2$, the total flow rate weighted average contamination $\eta_{tot}$ may follow the power-law decay model where the n-value is equal to 5/12. Accordingly, the total flow rate weighted average contamination may be expressed as follows:

$$\eta_{tot}(t + \Delta t) = \eta_{tot}(T_d) \cdot \left(\frac{t + \Delta t}{T_d}\right)^{-n} \quad \text{(EQ. 31)}$$

where $\eta_{tot,(T_d)}$ is the total flow rate weighted average contamination level at time $T_d$ when the sample contamination level first reaches the preset contamination level $\eta_{sd}$. Note that time t may be replaced by volume and $T_d$ may be replace with $v_d$ (e.g., pumped volume of formation fluid when the contamination level threshold $\eta_{sd}$ is reached).

Assuming the constraint in EQ. 22 and the following relationship:

$$\eta_g(t+\Delta t) < \eta_g(t) \quad \text{(EQ. 32)}$$

EQ. 9 may be reduced to the following:

$$Q_g(t + \Delta t) = \left(\frac{\eta_{tot}(t + \Delta t) - \eta_{sd}}{\eta_g(t) - \eta_{sd}}\right) Q_{tot}(t) \quad \text{(EQ. 33)}$$

Therefore, the data processing system 76 may use EQ. 33 to determine the guard flow rate $Q_g$ and the sample flow rate $Q_s$ (e.g., using EQ. 4) when n<5/12 and $t>T_d$. The total flow rate weighted average contamination level $\eta_{tot}(t+\Delta t)$ term in EQ. 33 may be determined based on EQ. 31. Similar to EQ. 20, the efficiency factor β may also be applied to EQ. 31.

In certain embodiments, the data processing system 76 may run a quality control test before determining the guard flow rate $Q_g$ and/or the sample flow rate $Q_s$. For example, selection of the efficiency factor β and/or the n-value (e.g., EQs. 27 and 31) may be done automatically by the data processing system 76 or may be manually entered by a user of the downhole acquisition tool 12. Therefore, there may be some sensitivity to the selection of the efficiency factor β and/or the n-value. The data processing system 76 may perform quality control on the guard flow rate equation(s) selected to determine the sample and guard flow rates $Q_s$ and $Q_g$, respectively, before filling the sample bottles. This may facilitate maintaining the sample line contamination at or below the preset contamination level $\eta_{sd}$ when the sample flow rate $Q_s$ and/or the guard flow rate $Q_g$ are adjusted to decrease the sample bottle filling times. The quality control test may include a time or volume based trial period once the sample contamination level reaches the preset contamination level threshold $\eta_{sd}$. As such, the quality control test may determine whether the efficiency factor β and/or the n-value selected are appropriate for determining optimal sample and guard flow rates $Q_s$ and $Q_g$, respectively, to decrease the sample bottle filling time. Additionally, the quality control test may allow validation of the constraints discussed above used to determine the guard flow rate $Q_g$. If the constraints are not appropriate, this may be an indication that plugging or other phenomena of the downhole acquisition tool 12 may be occurring.

As discussed above, the data processing system 76 may apply one or more algorithms to determine the sample and guard flow rates $Q_s$ and $Q_g$, respectively, that maintain the sample contamination level $\eta_s$ at or below the preset contamination level threshold $\eta_{sd}$, and decrease an amount of time to fill the sample bottles with formation fluid 52 that is representative of the native formation fluid 50. Returning to FIG. 4, once the data processing system 76 determines the sample and guard flow rates according to the acts of block 192, the method 180 includes adjusting the flow rate of the sampling probe 136 and the guard probe 138 (block 246) to decrease the sample bottle filling time while maintaining the sample contamination level $\eta_s$ at or below the preset contamination level threshold $\eta_{sd}$. For example, as discussed above, the sample flow rate $Q_s$ may be increased and the guard flow rate Qg may be decreased compared to the sample and guard flow rates at the start of clean-up. Therefore, by increasing the sample flow rate $Q_s$ and decreasing the guard flow rate $Q_g$ as determined by EQs. 7-9, 17, 19, 23, 25, 28, and/or 32, the sample and guard flow rate ratio may be such that the sample bottle filling time may be decreased without increasing the sample contamination level beyond the preset contamination level threshold $\eta_{sd}$ at a time after the earliest time $T_d$ the contamination level in the first fraction 148 reaches the preset contamination level threshold $\eta_{sd}$.

Figure 8:
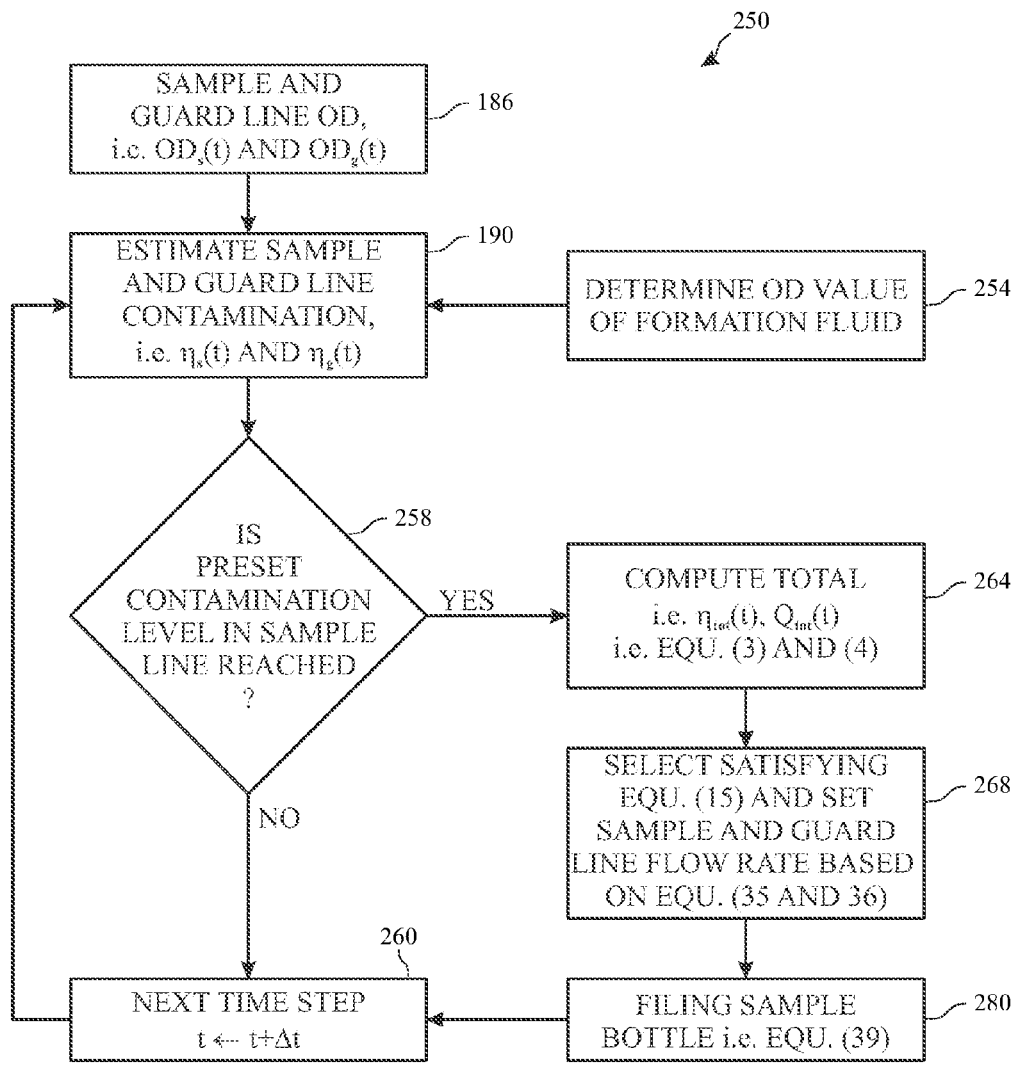
FIG. 8 is a flowchart depicting a method of decreasing a sample bottle filling time of the downhole acquisition tool of FIGS. 1 and 2, in accordance with one or more embodiments of the present disclosure.

FIG. 8 is a method 250 that may be used by the data processing system 76 to adjust the sample and guard flow rate, as discussed above. To facilitate discussion of the method 250, the method 250 will be discussed in the context of using optical density (OD) as the fluid property used to determine the contamination level of the formation fluid 52. However, any other fluid property (e.g., density, f-function (gas-to-oil ratio), resistivity, conductivity, compressibility, composition, etc.) may be used to determine the contamination level of the formation fluid 52. The method 250 includes calculating the optical density (OD) of the first fraction 148 and the second fraction 156 flowing through the sampling probe 136 and the guard probe 138 at time t (e.g., OD$_s$(t) and OD$_g$(t)), according to the acts of block 182 of the method 180, and estimating the mud filtrate contamination in the first fraction 148 and the second fraction 156 (e.g., η$_s$(t) and η$_g$(t)), according to the acts of block 186 of the method 180. The method 250 also includes determining the OD of the native formation fluid 52 (e.g., endpoint value); block 254. For example, the endpoint value may be determined by fitting a power-law decay model to the measured data and extrapolating the power-law decay model to infinity, as discussed above.

Following estimation of the contamination level in the fractions 148, 156 and the endpoint values, the method 250 includes a query 258 to determine whether the sample contamination level η$_s$ reached the preset contamination level threshold %$_a$ (e.g., is η$_s$≤η$_{sd}$). If the sample contamination level η$_s$ is not at or below the preset contamination level η$_{sd}$, the method 250 proceeds to the next time step t+Δt (block 260) and continues to estimate the sample and guard contamination levels η$_s$ and η$_g$ according to the acts of block 186. If the sample contamination level η$_s$ is at or below the preset contamination level η$_{sd}$, the data processing system 76 computes the total flow rate weighted average contamination level η$_{tot}$ and the total flow rate Q$_{tot}$ according to EQs. 3 and 4 (block 264).

Once the data processing system 76 determines the total flow rate weighted average contamination level η$_{tot}$ and the total flow rate Q$_{tot}$, the method 250 includes selecting α such that α satisfies the constraints in EQ. 15 and setting the sample and guard flow rates Q$_s$ and Q$_g$, respectively (block 268): In certain embodiments, the sample and guard flow rates may be set based on the following relationships $$Q_g(t + \Delta t) = \alpha \left( \frac{\eta_g(t) - \eta_{sd}}{\eta_{tot}(t) - \eta_{sd}} \right) \frac{Q_{tot}(t + \Delta)}{Q_{tot}(t)} Q_g(t) \quad \text{(EQ. 34)}$$

$$Q_s(t + \Delta t) = Q_{tot}(t + \Delta t) - Q_g(t + \Delta t) \quad \text{(EQ. 35)}$$

Figure 9:
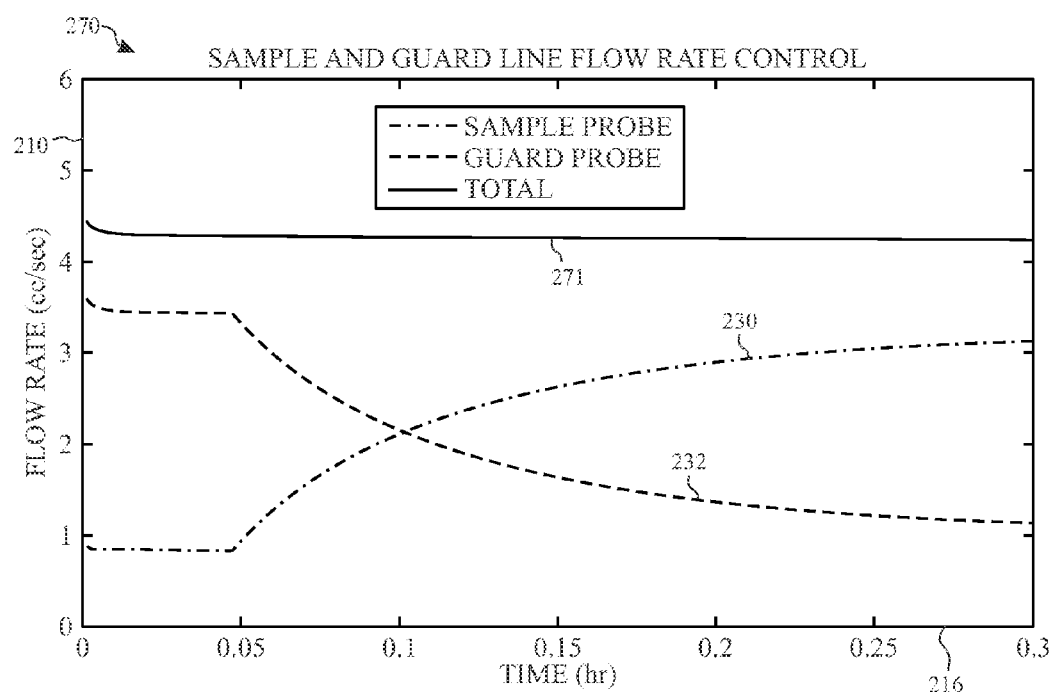
FIG. 9 depicts a graph reflecting a relationship between contamination of a first portion of the formation fluid in a sample probe and a second portion of formation fluid in a guard probe as analyzed by a focused sampling tool and pump-out time when a contamination level of the first portion is at or below a preset contamination threshold, in accordance with one or more embodiments of the present disclosure.

For example, FIG. 9 illustrates a representative plot 270 of the flow rate 210 as a function of time 216 in hours (hr). As illustrated in the plot 270, the sample contamination level η$_s$ reaches the preset contamination level threshold η$_{sd}$ at approximately 0.05 hours after the start of clean-up, as evidenced by the increase in the sample flow rate 228 and the decrease in the guard flow rate 230 at approximately 0.05 hours. While the flow rates 228, 230 change once the sample contamination level η$_s$ reaches the preset contamination level threshold η$_{sd}$, the overall flow rate 271 of the downhole acquisition tool 12 remains substantially constant over time. The combination of the flow rate change in the sample probe 136 and the guard probe 138 results in a sample and guard flow rate ratio that may maintain the sample contamination level η$_s$ at or below the preset contamination level threshold η$_{sd}$, as shown in FIGS. 5 and 6.

In other embodiments, the data processing system 76 may use the optical density (OD) or other suitable fluid properties rather than the contamination levels (e.g., η$_g$, η$_{tot}$, and η$_{sd}$) to set the sample and guard flow rates based on the following relationships:

$$Q_g(t + \Delta t) = \alpha \left( \frac{OD_g(t) - OD_{sd}}{OD_{tot}(t) - OD_{sd}} \right) \frac{Q_{tot}(t + \Delta)}{Q_{tot}(t)} Q_g(t) \quad \text{(EQ. 36)}$$

-continued $$Q_g(t + \Delta t) = \alpha \left( \frac{\rho_g(t) - \rho_{sd}}{\rho_{tot}(t) - \rho_{sd}} \right) \frac{Q_{tot}(t + \Delta)}{Q_{tot}(t)} Q_g(t) \quad \text{(EQ. 37)}$$

Following selection of α and setting of the sample and guard flow rates, the method 250 includes filling the sample bottle with the first fraction 148 (block 280). The data processing system 76 may monitor the volume of the sample bottle during filling according to the following relationship:

$$V_r(t) = V_s - \int_{T_d}^{t} Q_s(\tau) d\tau \quad \text{(EQ. 38)}$$

where

V$_s$ is the sample bottle volume

Figure 10:
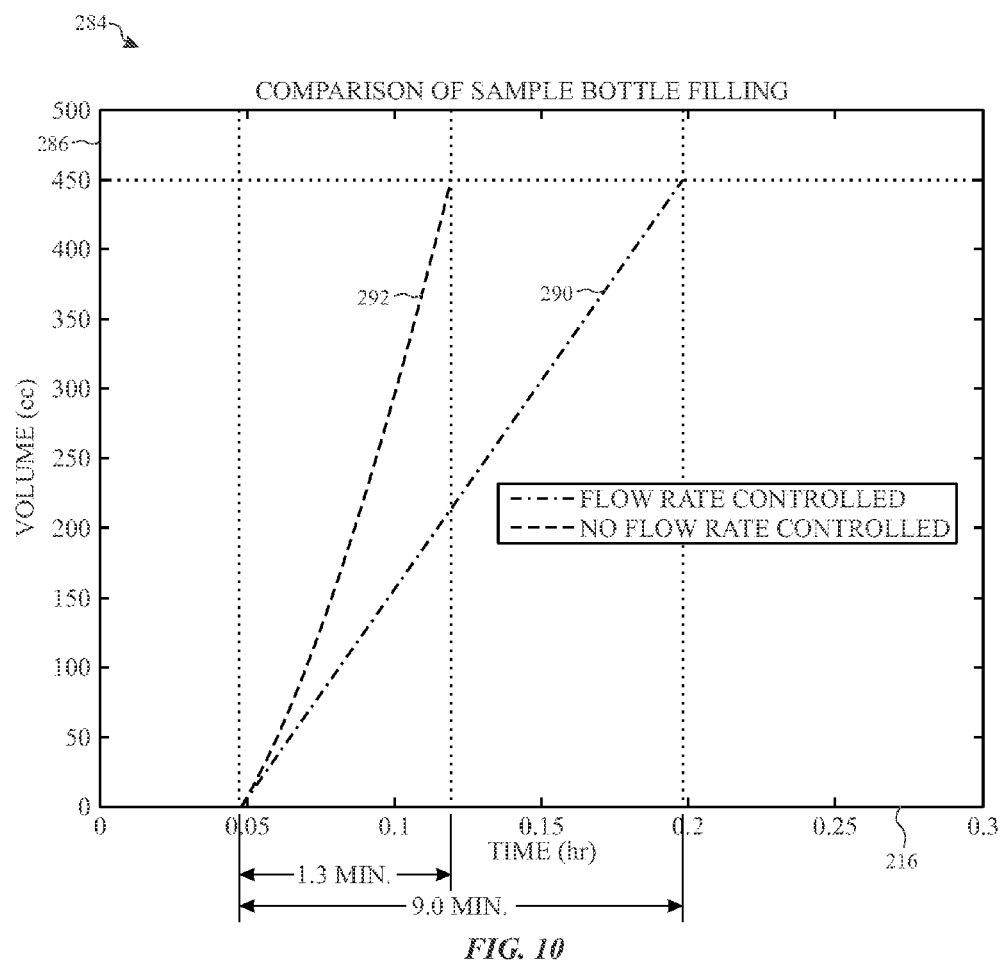
FIG. 10 depicts a graph comparing sample bottle filling times using the sample probe with and without adjustment of the sample probe and guard probe flow rates after the first portion of the formation fluid reaches the preset contamination level threshold, in accordance with one or more embodiments of the present disclosure.

V$_r$(t) is the remaining sample bottle volume up to time t. For example, FIG. 10 illustrates a plot 284 of volume 286 in cubic centimeters (cc) as a function of the time 216. For a given sample bottle of approximately 450 cc, non-flow rate adjusted sample bottle filling 290 took approximately 9 minutes to fill the sample bottle. In contrast, by adjusting the sample and guard flow rates based on EQs. 8-10, 18, 20, 24, 26, 29, and/or 33-35, as discussed above, the sample bottle filling time may be decreased between approximately 40% and approximately 60%. For example, as shown in plot 284, flow rate adjusted sample bottle filling 292 was completed in approximately half the time (e.g. approximately 4.3 minutes) it took the non-flow rate adjusted sample bottle filling 290.

As discussed above, and shown in the data presented herein, the disclosed techniques for controlling the flow rates of the sampling probe 136 and the guard probe 138 after the sample contamination level η$_s$ reaches the preset contamination level threshold η$_{sd}$ results in a decrease in the sample bottle filling time compared to sample bottle filling time techniques that do not adjust the sample and guard flow rates. By controlling the sample and guard flow rates such that the sample flow rate Q$_s$ is increased while the guard flow rate Q$_g$ is decreased, the sample bottle filling times may be decreased without increasing the sample contamination level η$_s$ above the preset contamination level threshold η$_{sd}$. Accordingly, rig time and operational costs associated with collecting representative samples of the native formation fluid 50 may be decreased compared to sampling techniques that do not adjust both sample and guard flow rates.

The specific embodiments described above have been shown by way of example, and it should be understood that these embodiments may be susceptible to various modifications and alternative forms. It should be further understood that the claims are not intended to be limited to the particular forms discloses, but rather to cover modifications, equivalents, and alternatives falling within the spirit of this disclosure.

The invention claimed is:

1. A method comprising:
    operating a downhole acquisition tool comprising a guard probe and a sample probe in a wellbore in a geological formation, wherein the wellbore or the geological formation, or both contains a fluid that comprises a native reservoir fluid of the geological formation and a contaminant;
    receiving a first portion of the fluid into the guard probe and a second portion of the fluid into the sample probe;
    estimating a contamination level of the first portion of the fluid, the second portion of the fluid, or a combination thereof based on a fluid property of the respective first and second portions of the fluid as measured by the downhole acquisition tool;

determining an initial guard flow rate of the first portion of fluid through the guard probe;

determining an initial sample flow rate of the second portion of fluid through the sample probe;

using a processor to:

adjust a guard flow rate of the second portion of the fluid through the guard probe over pump time after the contamination level of the first portion of the fluid is at or below a contamination level threshold, based on the initial guard flow rate and a cumulative contamination level of the first and second portion of the fluid; and adjust a sample flow rate of the first portion of the fluid through the sample probe based on the adjusted guard flow rate and the total flowrate.

2. The method of claim 1, wherein the cumulative contamination level is a weighted average contamination of the fluid over the pump time, wherein the guard flow rate is further determined based on the weight rated contamination of the fluid.

3. The method of claim 1, wherein determining the guard flow rate further comprises applying a guard efficiency factor to correct for changes in guarding efficiency of the guard probe.

4. The method of claim 1, wherein determining the guard flow rate accords with the following relationship:

$$Q_g(t + \Delta t) = \left( \frac{\eta_{tot}(t) - \eta_{sd}}{\eta_g(T_d)\left(\frac{t+\Delta t}{T_d}\right)^{-n} - \eta_{sd}} \right) Q_{tot}(t)$$

where $Q_g$ represents the guard flow rate of the guard probe;

$Q_{tot}$ represents a total flow rate of the downhole acquisition tool;

$\eta_{tot}$ represents a total flow rate weighted average contamination level of the fluid;

$\eta_{sd}$ represents a contamination level threshold of the first portion of the fluid;

$T_d$ represents the earliest time the contamination level of the first portion reaches the contamination level threshold;

n represents a parameter of the probe sampling or an adjustment parameter; and t represents pump-out time of the first and second portions of the fluid.

5. The method of claim 4, wherein time is replaced by pumpout volume.

6. The method of claim 1, wherein determining the guard flow rate accords with the following relationship:

$$Q_g(t + \Delta t) = \left( \frac{\eta_{n_{tot}}(t) - \eta_{n_{sd}}}{\eta_{n_g}(T_d)\left(\frac{t+\Delta t}{T_d}\right)^{-n} - \eta_{n_{sd}}} \right) Q_{tot}(t)$$

where $Q_g$ represents the guard flow rate of the guard probe;

$Q_{tot}$ represents a total flow rate of the downhole acquisition tool;

$\eta_g$ represents a guard flow rate of the second portion of the fluid;

$\eta_{tot}$ represents a total flow rate weighted average contamination level of the fluid;

$\eta_{sd}$ represents a contamination level threshold of the first portion of the fluid;

$T_d$ represents the earliest time the contamination level of the first portion reaches the contamination level threshold;

n represents a parameter of the probe sampling or an adjustment parameter and t represents pump-out time of the first and second portions of the fluid.

7. The method of claim 6, wherein time is replaced by pumpout volume.

8. The method of claim 1, wherein the guard flow rate of the second portion of the fluid is less than the initial guard flow rate and the sample flow rate of the first portion is greater than the initial sample flow rate.

9. The method of claim 1, comprising filling a sample bottle of the downhole acquisition tool with the first portion of the fluid after adjusting the sample flow rate, wherein the sample flow rate is greater than the initial sample flow rate.

10. The method of claim 1, wherein the contaminant comprises an oil-based mud or a water-based mud.

11. The method of claim 1, wherein the first portion of the fluid is representative of the native reservoir fluid when the contamination level of the first portion of the fluid is at or below the contamination level threshold.

12. A downhole fluid testing system comprising:

a downhole acquisition tool housing configured to be moved into a wellbore in a geological formation, wherein the wellbore or the geological formation, or both, contains a fluid that comprises a native reservoir fluid of the geological formation and a contaminant;

a plurality of sensors disposed in the downhole acquisition tool housing that are configured to analyze portions of a first portion of the fluid and a second portion of the fluid and obtain sets of fluid properties of the first and second portions of the fluid;

a guard probe configured to flow the first portion of the fluid at a guard flow rate;

a sample probe configured to flow the second portion of the fluid at a sample flow rate; and a data processing system configured to:

adjust the guard flow rate over pump time of the fluid, after a contamination level of the first portion of the fluid is at or below a contamination level threshold, based on a total flow rate weighted average fluid property of the first portion of the fluid and the second portion of the fluid and an initial guard flow rate, an initial sample flow rate, or both, wherein the total flow rate weighted average fluid property comprises the fluid property of the first portion of the fluid and the fluid property second portion of the fluid measured over the pump time; and adjust the sample flow rate based on the adjusted guard flow rate and the total flow rate.

13. The system of claim 12, wherein the data processing system is disposed within the downhole acquisition tool housing, or outside the downhole acquisition tool housing at the surface, or both.

14. The system of claim 12, comprising a sample bottle disposed within the downhole acquisition tool, wherein the sample probe is fluidly coupled to the sample bottle and configured to direct the second portion of the fluid to the sample bottle.

15. The system of claim 12, wherein the data processing system determines the guard flow rate based on the following relationship:

$$Q_g(t+\Delta t) = \left( \frac{FT(t) - FP_{sd}}{FP_g(T_d)\left(\frac{t+\Delta t}{T_d}\right)^{-n} - FP_{sd}} \right) Q_{tot}(t)$$

where $Q_g$ represents the guard flow rate of the guard probe;

$Q_{tot}$ represents a total flow rate of the downhole acquisition tool;

$FP_{tot}$ represents the total flow rate weighted average fluid property of the fluid;

$FP_{sd}$ represents a fluid property threshold of the first portion of the fluid;

$FP_g$ represents a fluid property threshold of the second portion of the fluid;

$T_d$ represents the earliest time the fluid property of the first portion reaches the fluid property threshold;

n represents a parameter of the probe sampling or an adjustment parameter and t represents pump-out time of the first and second portions of the fluid.

16. The system of claim 15, wherein time is replaced by pumpout volume.

17. The system of claim 12, wherein the data processing system determines the guard flow rate based on the following relationship:

$$Q_g(t+\Delta t) = \left( \frac{FP_{tot}(T_d)\left(\frac{t+\Delta t}{T_d}\right)^{-n} - FP_{sd}}{FP_g(t) - FP_{sd}} \right) Q_{tot}(t)$$

where $Q_g$ represents the guard flow rate of the guard probe;

$Q_{tot}$ represents a total flow rate of the downhole acquisition tool;

$FP_{tot}$ represents the total flow rate weighted average fluid property;

$FP_{sd}$ represents a fluid property threshold of the first portion of the fluid;

$FP_g$ represents a fluid property threshold of the second portion of the fluid;

$T_d$ represents the earliest time the fluid property of the first portion reaches the fluid property threshold;

n represents a parameter of the probe sampling or an adjustment parameter; and t represents pump-out time of the first and second portions of the fluid.

18. The system of claim 17, wherein time is replaced by pumpout volume.

19. The system of claim 12, wherein the data processing system applies a guard efficiency factor when determining the guard flow rate to correct for changes in guarding efficiency of the guard probe.

20. One or more tangible, non-transitory, machine-readable media comprising instructions to:

receive a plurality of fluid parameters of a first portion and a second portion of a fluid as analyzed by a downhole acquisition tool in a wellbore in a geological formation, wherein the wellbore or the geological formation, or both, contains the fluid, wherein the fluid comprises a mixture of native reservoir fluid of the geological formation and a contaminant;

determine an initial guard flow rate of the first portion of the fluid flowing through a guard probe of the downhole acquisition tool;

determine an initial sample flow rate of the second portion of the fluid flowing through a sample probe of the downhole acquisition tool;

determine a guard flow rate of the first portion of the fluid over pump time based on a cumulative contamination level of the second portion of the fluid and the initial guard flow rate; and adjust a sample flow rate of the second portion of the fluid based on a relationship between the guard flow rate and a total flow rate of the fluid through the downhole acquisition tool when the contamination level of the first portion of the fluid is at or below a contamination level threshold.

21. The one or more tangible, non-transitory, machine-readable media of claim 20, comprising instructions to determine the guard flow rate according to the following relationship $$Q_g(t+\Delta t) = \left( \frac{\eta_{n_{tot}}(t) - \eta_{n_{sd}}}{\eta_{n_g}(T_d)\left(\frac{t+\Delta t}{T_d}\right)^{-n} - \eta_{n_{sd}}} \right) Q_{tot}(t)$$

where $Q_g$ represents the guard flow rate of the guard probe;

$Q_{tot}$ represents a total flow rate of the downhole acquisition tool;

$\eta_g$ represents a guard flow rate of the second portion of the fluid;

$\eta_{tot}$ represents a total flow rate weighted average contamination level of the fluid;

$\eta_{sd}$ represents a contamination level threshold of the first portion of the fluid;

$T_d$ represents the earliest time the contamination level of the first portion reaches the contamination level threshold;

n represents a parameter of the probe sampling or an adjustment parameter; and t represents pump-out time of the first and second portions of the fluid.

22. The one or more tangible, non-transitory, machine-readable media of claim 20, comprising instructions to determine the guard flow rate based on a weight rated contamination of the fluid.

23. The one or more tangible, non-transitory, machine-readable media of claim 20, comprising instructions to apply a guard efficiency factor when determining the guard flow rate to correct for changes in guarding efficiency of the guard probe.

* * * * *